(12) United States Patent
Gauchet et al.

(10) Patent No.: US 6,527,804 B1
(45) Date of Patent: Mar. 4, 2003

(54) INTERVERTEBRAL DISK PROSTHESIS

(75) Inventors: Fabien Gauchet, Route de Rocquemont (FR); Régis Le Couedic, Cestas (FR)

(73) Assignee: DIMSO (Distribution Medicale du Sud-Quest) (FR)

( * ) Notice: Subject to any disclaimer, the term of this patent is extended or adjusted under 35 U.S.C. 154(b) by 0 days.

(21) Appl. No.: 09/857,659

(22) PCT Filed: Dec. 9, 1999

(86) PCT No.: PCT/FR99/03072
§ 371 (c)(1),
(2), (4) Date: Jul. 20, 2001

(87) PCT Pub. No.: WO00/35384
PCT Pub. Date: Jun. 22, 2000

(30) Foreign Application Priority Data

Dec. 11, 1998 (FR) .............................. 98 15671

(51) Int. Cl.[7] .................................................. A61F 2/44
(52) U.S. Cl. ................. 623/17.12; 623/17.15; 623/17.16
(58) Field of Search ........................ 623/17.12, 17.13, 623/17.15, 17.16, 17.11

(56) References Cited

U.S. PATENT DOCUMENTS

| 3,875,595 A | * | 4/1975 | Froning .................. 623/17.12 |
| 4,932,969 A | | 6/1990 | Frey et al. |
| 5,123,926 A | * | 6/1992 | Pisharodi |
| 5,401,269 A | | 3/1995 | Buttner-Janz et al. |
| 5,674,294 A | | 10/1997 | Bainville et al. |
| 6,395,032 B1 | * | 5/2002 | Gauchet .................. 623/17.12 |

FOREIGN PATENT DOCUMENTS

| DE | 2 263 842 | | 7/1974 | |
| DE | 3741493 A | * | 6/1989 | .................. 623/17 |
| DE | 9000094.3 | | 3/1991 | |
| EP | 0356112 B1 | | 12/1993 | |
| FR | 2 723 841 | | 3/1996 | |

OTHER PUBLICATIONS

English Translation of French No. 2,723,841.*
09/857,726 Gauchet Et Al. filed Jul. 20, 2001.

* cited by examiner

Primary Examiner—Jeffrey A. Smith
(74) Attorney, Agent, or Firm—Lerner, David, Littenberg, Krumholz & Mentlik, LLP

(57) ABSTRACT

An intervertebral disc prosthesis comprising two plates and a cushion interposed between the plates is contemplated. The cushion includes a compressible body having two ends in contact with the plates. At least one of the ends is freely displaceable relative to the plate in a parallel direction. Thus, the prosthesis imitates and approximates the mechanical properties of a healthy natural intervertebral disc.

21 Claims, 3 Drawing Sheets

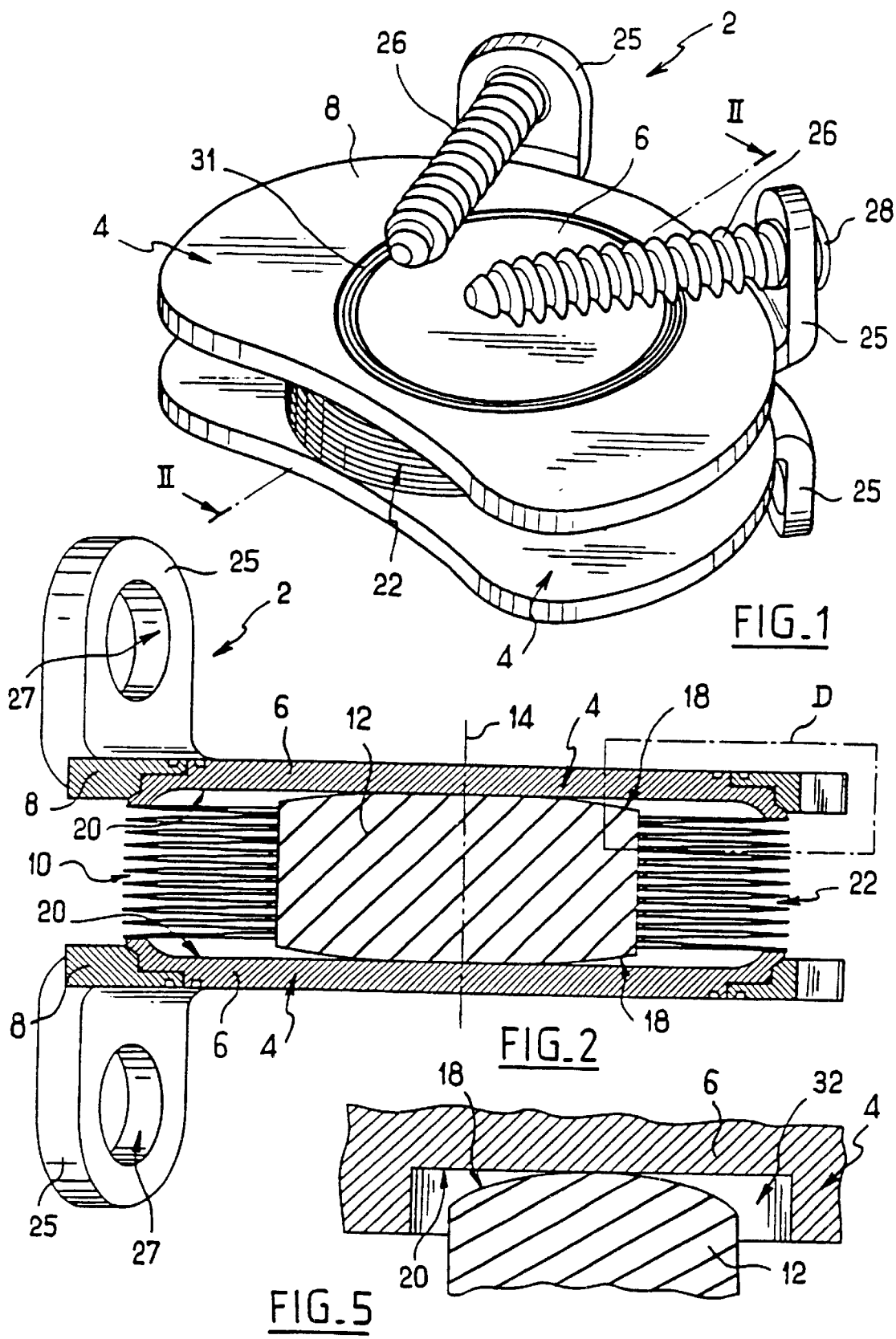

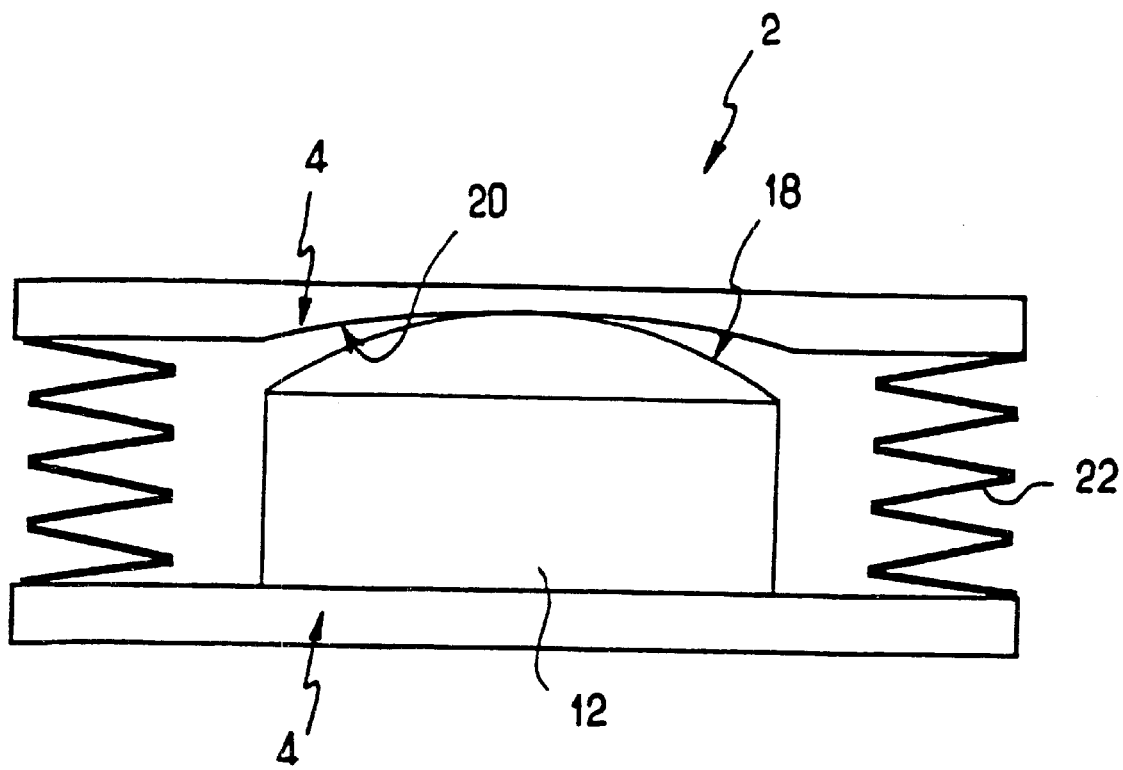
FIG_6

INTERVERTEBRAL DISK PROSTHESIS

FIELD OF THE INVENTION

The invention relates to intervertebral disk prostheses.

European Patent No. 277 282-Al discloses an intervertebral disk prosthesis, comprising two plates and a cushion interposed between them. The cushion comprises a compressible body delimiting a cavity filled with an incompressible fluid. This prosthesis is essentially incompressible in the axial direction and allows only a relative inclination of the plates. This behavior is different from that of a healthy, natural intervertebral disk.

An object of the invention is to provide a disk prosthesis which more closely imitates and approximates the mechanical properties of a healthy, natural intervertebral disk.

SUMMARY OF THE INVENTION

With a view to achieving this object, according to the invention an intervertebral disk prosthesis is envisaged comprising two plates and a cushion interposed between the plates, the cushion comprising a compressible body and containing a fluid, which is compressible.

Thus the compression of the cushion affects the compression of the body and the fluid. Since the compression properties of the body and the fluid can be different, their combination allows a very close approximation to the mechanical properties of a healthy, natural intervertebral disk. More particularly, when the body is made of suitable material, the curve of the mechanical reaction to a compression of the cushion as a function of a variation in a dimension of the cushion in the direction of compression can be obtained, having a hysteresis shape close to that associated with a healthy, natural disk.

Advantageously, the fluid has a pressure such that it is more compressible than the body.

This difference can thus be utilized to approximate as closely as possible the mechanical properties of the healthy, natural disk.

Advantageously, the fluid comprises a gas.

Advantageously, the cushion is arranged such that a fluid pressure is applied directly to the plates.

Advantageously, the fluid extends around the periphery of the body.

Advantageously, the body comprises a viscoelastic material, preferably silicone.

The aforementioned curve, thus has a highly pronounced hysteresis shape can thus be obtained.

Advantageously, the body is in contact with the plates.

Advantageously, the body has at least one end having a contact zone with one of the plates, the prosthesis being arranged such that the contact zone has a surface area which increases whenever a stressing of the plate in the direction of the body is increased.

For the lowest compression values, the mechanical reaction of the prosthesis upon the compression of the body thus varies very little as a function of the dimensional change in the cushion in the direction of compression. In other words, the aforementioned curve is little inclined relative to the horizontal for low compression values and little force is provided in the initial operation. This property reproduces that of a healthy, natural disk.

Advantageously, the contact zone is defined by a face of the plate and an end face of the body, one of the two faces, typically the face of the body, being curved and convex and the other face being flat.

Advantageously, the contact zone is defined by a face of the plate and an end face of the body, the two faces being curved in at least one common direction and being respectively concave and convex, the concave face having at least one radius of curvature greater than a corresponding radius of curvature of the convex face.

As a result of this configuration, the variations in mechanical reaction, previously mentioned, can be effected. Moreover, when the body is free to shift laterally relative to the plate, as will be seen later, this configuration guarantees the relative centering of the two faces. For example, after the two faces have been mutually offset, these curvatures enable them to re-center automatically.

Advantageously, the body has at least one end in contact with one of the plates, this end being free to move relative to the plate in a direction parallel to the plate.

Advantageously, the end is accommodated in a recess of the plate and forms a lateral abutment for the body.

The lateral displacements of the body relative to the plates can thus be limited, or even barred.

Advantageously, the cushion comprises a shell containing the fluid and arranged such that it has a cross-sectional area parallel to the plates which is essentially invariable when variation occurs in a compression of the cushion between the plates.

Advantageously, the cushion comprises a chamber containing the fluid and extending around the periphery of the body at a distance.

The erosion of the body by the chamber in the course of its movement and the dispersion of particles of the body are thus prevented.

Advantageously, the chamber forms a spring, especially a compression spring.

The chamber thus influences the reaction of the cushion whenever this is compressed.

Advantageously, the cushion is arranged to exhibit a hysteresis-shaped curve of mechanical reaction to a compression as a function of a variation in a dimension of the cushion in the direction of the compression.

Advantageously, the cushion is arranged such that the reaction to the compression grows less markedly for relatively low reaction values than for relatively high reaction values.

Advantageously, the cushion is arranged such that the reaction to the compression diminishes more markedly for relatively high reaction values than for relatively low reaction values.

Advantageously, the cushion is arranged such that the reaction to the compression has higher values when it grows than when it diminishes.

Advantageously, the prosthesis is intended for the lumbar region of the spine.

Other characteristics and advantages of the invention are yet to appear in the following description of the preferred embodiments, given by way of non-limiting examples.

BRIEF DESCRIPTION OF THE DRAWINGS

FIG. 1 is a perspective view of a prosthesis according to the invention;

FIG. 2 is a axial section along the plane II—II of the prosthesis of FIG. 1;

FIG. 5 is a sectional view of a detail of an illustrative embodiment of the prosthesis; and FIG. 6 is a simplified view analogous to FIG. 2 showing a second illustrative embodiment.

DETAILED DESCRIPTION OF THE INVENTION

Figure 3:
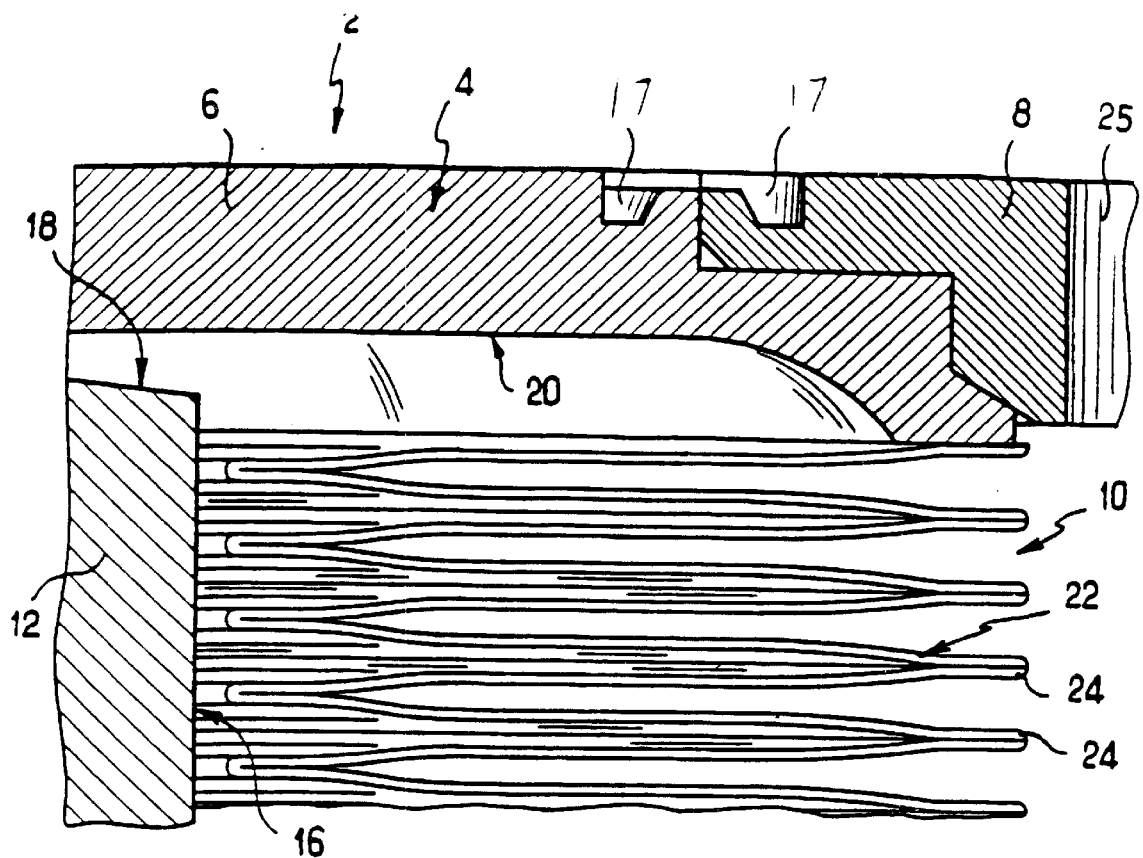
FIG. 3 is an enlarged scale view of a detail D of FIG. 2.

FIG. 1 shows an intervertebral disk prosthesis 2 according to the invention particularly intended for the lumbar region of the vertebral column of the human body. The prosthesis 2 comprises two flat plates 4 having the general shape of a bean with a posterior hilum in plan view. Each plate 4 comprises a central circular panel 6 and a border 8 extending about the periphery of the panel 6 in the plane thereof. At rest, the two plates 4 extend parallel to each other, at a distance facing each other with their contours in alignment. On each plate 4, the border 8 and the panel 6 each have a groove 17 for the reception of a seal.

The disk prosthesis 2 comprises a cushion or intermediate part 10 interposed between the two plates 4. The cushion comprises a compressible solid body 12, here made of viscoelastic material, for example silicone. This body has a Shore-A hardness advantageously 60 to 100, in this case approximately 80. The body 12 has a shape of revolution about its main axis 14. It has a cylindrical lateral face 16 and two axial end faces 18 generally perpendicular to the axis 14 and of slightly convex spherical shape. Each face 18 thus has two identical curvatures in mutually perpendicular planes. The body 12 is disposed coaxially with the panels 6. Each panel 6 has a plane inner central face 20 perpendicular to the axis 14 and in contact with one of the respective axial ends 18 of the body 12. Thus, the convex spherical face 18 of the body rests on the plane face 20 of the plate. The body 12 rests without anchorage on each of the plates 4 such that it is movable relative to each of these plates in a direction parallel to the plates, that is to say perpendicular to the main axis 14. Given the compression of the body 12 exerted by the plates 4, and the form of the faces of the plates and the body, the mobility in this direction is manifested by a rolling movement, optionally without sliding, of each axial end 18 of the body on the face 20 of the plate with which it is in contact. The body thus rolls between the two plates. The two plates are thus laterally displaced relative to each other while remaining parallel, if necessary. The transmission of lateral stresses from the one to the other of the vertebrae is thus prevented.

The cushion 10 additionally comprises a bellows 22. The bellows coaxially surrounds the body 14 at a distance therefrom. The bellows 22 has a symmetrical shape in revolution about the axis 14. Its wall profile comprises corrugations 24 allowing the length of the bellows 22 to be varied in the axial direction 14 without any appreciable variation in the surface area of its cross section transverse to the axis 14. The bellows 22, like the plates 4, may be made of titanium or titanium alloy, so that it has a certain axial rigidity and forms a compression spring. The bellows can also be deformed in a direction perpendicular to the axis 14 or can be twisted about the axis 14 or about any axis perpendicular thereto.

At its two axial ends, the bellows 22 has edges bonded to respective edges of the panels 6 projecting from the inner face 20. The bonding is leaktight so that the bellows 22 and the two panels 6 define a variable-volume, leaktight chamber extending around the body 12. This chamber contains a fluid, for example a gas, such as air. The undulations 24 nearest to the body 12 extend at a distance from the latter to allow a free circulation of gas from the one to the other of the dishes 6.

As shown, the bellows 22 has ten convolutions, with eight outer crests in addition to two crests for securement to the plates. The outer diameter is about 30 mm and the inner diameter is about 17 mm. Its height, when the prosthesis is not bonded, measures about 10 mm. The wall of the bellows can be produced by means of one, two or three sheets, each measuring about 0.1 mm thick. The sum of the thicknesses of the sheets forms the thickness of the wall. The bellows here has an inherent strength of around 1.6 N/mm.

Each border 8 comprises two lugs 25 projecting from an outer face of the plate 4 perpendicularly to the plane of the plate. Each lug 25 has an orifice 27 traversing through it in the direction of the center of the plane and, a spherical recess directed away from the plate 4 on one face of the lug 25. The orifices 27 are able to receive a bone screw 26 having a head 28, whose lower face has a male spherical shape cooperating with the female recess of the lug 25 to allow free orientation of the screw 26 relative to the associated lug.

For short-term anchoring of the disc prosthesis 2 in the spine, the screws 26 can be anchored in the spondylus of the vertebrae adjacent to the disk to be replaced.

A "long term" anchorage might be envisaged, in which the surfaces of the plates 4 in contact with the adjacent vertebrae are covered with hydroxyapatite, or with any other substance known per se for stimulating bone growth. Prior to being covered, the surfaces can be treated to obtain a more or less porous surface condition, with anchoring points for the bone tissue, in order to ensure a better interface with the bone tissue.

Figure 4:
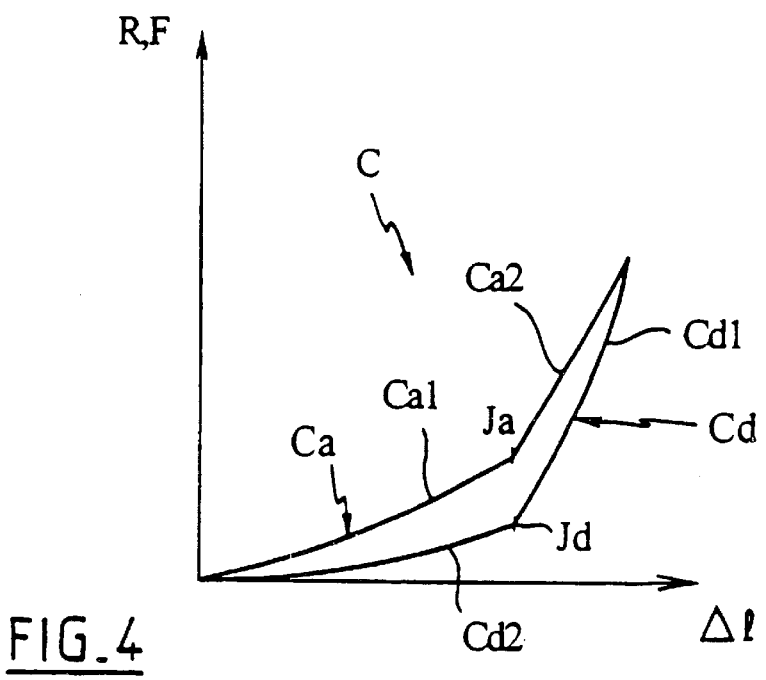
FIG. 4 is a curve indicating the compression force F applied by th o plates to the cushion as a function of the variation in the distance separating them.

FIG. 4 shows the path of the curve C, indicating the intensity of a compression force F exerted on the cushion 10 (that is to say on the two plates 4), disregarding their deformability, which is virtually nil, in the axial direction 14, as a function of the variation in length 1 of the cushion in the axial direction 14 (or in the distance between the two plates). This curve also represents the mechanical reaction R of the cushion 10 under the same conditions.

This curve C is not linear. Moreover, it has a hysteresis form: the curve Ca indicating the increase in the compression F from the zero origin being distinct from the curve Cd indicating the decrease in the compression F up to the origin, and extending entirely above it. This pronounced hysteresis form is due principally to the viscoelastic material of the body and secondarily to the combination of the body 12 and the fluid in the cushion 10.

In addition, the curve Ca, relating to the increase in the compression force F, exhibits a gently sloping portion Ca1 from the origin O, then a more heavily sloping portion Ca2. The curve Cd illustrating the decrease in the compression F exhibits for the highest values of the force F a markedly sloping portion Cd1, then for the lowest values of the force F a more gently sloping portion Cd2. The presence of a gently sloping portion in the vicinity of the origin for the curves Ca and Cd is due principally to the configuration of the contact faces 18, 20 of the body 12 and of the plates 4, the effect of which is to increase the surface area of the mutual contact zone between each plate and the body, generally in the form of a disk, whenever the force F is increased. This increase occurs until the maximum surface area of the contact zone is reached, when the whole of the face 18 is touching the plate 4.

The connecting points Ja and Jd respectively form the junction between the curves Ca1 and Ca2 and Cd1 and Cd2. On the curve Ca, the point Ja corresponds to the force F at which the maximum contact surfaces between the plates and the body are reached. Likewise, on the curve Cd, the point Jd corresponds to the force at which these surfaces cease to be at a maximum.

The prosthesis can be configured such that the point Ja corresponds to a value of Δl between 25% and 75% of the maximum variation in length envisaged for the prosthesis during use.

Referring to FIG. 5, in an alternate embodiment, (otherwise having the other characteristics of the prosthesis of FIG. 1) the face 20 of each plate 4 opposite the body 12 has a recess 32, in this case, a U-shaped recess, forming a lateral abatement, in which the corresponding axial end 18 of the body fits. The relative lateral displacements of the body 12 with respect to each plate 4 are thus limited to a certain range, or even totally barred.

In the alternate embodiment shown in FIG. 6, the face 20 can be curved and concave in one or both directions, as shown, and the face 18 can be curved and convex in the corresponding direction(s), the radius of curvature of the face 20 being, for each direction, greater than that of the face 18 in the corresponding direction. The two faces 18, 20 are spherical as shown. The radii of curvature of the surfaces 18 and 20 will, for example, be within the range of about 70 to about 80 mm, and between about 140 to about 200 mm respectively. Such an arrangement allows the two faces to be centered automatically, while at the same time permitting a relative lateral displacement of the body 12 relative to the plate in any direction whatsoever perpendicular to a longitudinal direction of the spine.

In the embodiment shown in FIG. 2, the two ends of the body 12 have a contact surface 18 with the associated plate of variable surface area, making it laterally movable relative to the body.

By contrast, in the alternate embodiment shown in FIG. 6, only one of the ends 18 of the body 12 exhibits this property. The other end, being the lower end in FIG. 6, has a plane circular shape with an invariable contact zone with the associated plate and fixed relative to the latter.

Of course, numerous modifications might be made to the invention without departing from the scope thereof.

The fluid might be a liquid, or even a mixture of a liquid and a gas, the latter being, for example, weakly soluble in the liquid.

The body might have an elliptical shape in cross section to the axis 14.

The inner face 20 of the plates 4 might be convex, the axial end face 18 of the body 12 being flat, or concave with a greater radius of curvature than that of the face 20 of the plate. The two contacting faces of the plate and the body might be convex.

The curvature of the faces might be limited to a single plane.

The characteristics relating to the envelope 22 (spring effect, distance to the body 12) might be effected independently of the other characteristics.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Intervertebral disc prosthesis, comprising:

tow plates; and a cushion interposed between the plates, the cushion comprising a compressible body including a compressible fluid, wherein the fluid extends around the periphery of the body.

2. Prosthesis according to claim 1, wherein the fluid comprises a gas.

3. Prosthesis according to claim 1, wherein the cushion is arranged such that a fluid pressure is applied directly to the plates.

4. Prosthesis according to claim 1, wherein the cushion exhibits a hysteresis-shaped curve of mechanical reaction to a compression as a function of a variation in a dimension of the cushion in the direction of the compression.

5. Prosthesis according to claim 4, wherein the cushion reaction to the compression is less for relatively low reaction values than for relatively high reaction values.

6. Prosthesis according to claim 4 or 5, wherein the cushion reaction to the compression diminishes more for relatively high reaction values than for relatively low reaction values.

7. Prosthesis according to claim 4 or 5, wherein the cushion reaction to the compression has higher values when the cushion grows than when it diminishes.

8. Prosthesis according to claim 1, wherein the prosthesis is a lumbar intervertebral disk prosthesis.

9. Intervertebral disc prosthesis, comprising:

two plates; and a cushion interposed between the plates, the cushion comprising a compressible body and including a compressible fluid, wherein the fluid has a pressure such that the fluid is more compressible than the body.

10. Intervertebral disc prosthesis, comprising:

two plates; and a cushion interposed between the plates, the cushion comprising a compressible body made from a viscoelastic material and including a compressible fluid.

11. Prosthesis according to claim 10, wherein the viscoelastic material is silicone.

12. Intervertebral disc prosthesis, comprising:

two plates; and a cushion interposed between the plates, wherein the cushion comprises a compressible body and includes a compressible fluid, and wherein the body has at least one end defining a contact zone with one of the plates and the prosthesis is arranged such that the contact zone has a surface area which increases whenever a stressing of the plates in the direction of the body is increased.

13. Prosthesis according to claim 12, wherein the contact zone is defined by a face of the plate and an end face of the body, one of the faces being curved and convex and the other face being flat.

14. Prosthesis according to claim 13, wherein the end face of the body is curved and convex and the face of the plate is flat.

15. Prosthesis according to claim 12, wherein the contact zone is defined by a face of the plate and an end face of the body, the plate face and the body face being curved in at least one common direction and being concave and convex, the concave face having at least one radius of curvature greater than a corresponding radius of curvature of the convex face.

16. Intervertebral disc prosthesis, comprising:

two plates; and a cushion interposed between the plates, wherein the cushion comprises a compressible body and includes a compressible fluid, and wherein the body has at least one end in contact with one of the plates, the at least one end being free to move relative to the plate in a direction parallel to the plate.

17. Prosthesis according to claim 16, wherein the end is accommodated in a recess of the plate forming a lateral abutment for the body.

18. Intervertebral disc prosthesis, comprising:

two plates; and a cushion interposed between the plates, wherein the cushion comprises a compressible chamber containing a compressible fluid such that the chamber has a cross-sectional area parallel to the plates which is essentially invariable when variation occurs in a compression of the cushion between the plates.

19. Intervertebral disc prosthesis, comprising:

two plates; and a cushion interposed between the plates, wherein the cushion comprises a compressible chamber containing a compressible fluid and extending around the periphery of the body and a distance from the body.

20. Prosthesis according to claim 18 or 19, wherein the chamber forms a spring.

21. Prosthesis according to claim 20, wherein the spring is a compression spring.

* * * * *

UNITED STATES PATENT AND TRADEMARK OFFICE
CERTIFICATE OF CORRECTION

PATENT NO.   : 6,527,804 B1
DATED        : March 4, 2003
INVENTOR(S)  : Fabien Gauchet and Le Couedic Regis It is certified that error appears in the above-identified patent and that said Letters Patent is hereby corrected as shown below:

<u>Title page,</u>
Item [73], Assignee, "Sud-Quest" should read -- Sud-Ouest --.

<u>Column 1,</u>
Line 49, "curve, thus has" should read -- curve having --.

<u>Column 2,</u>
Line 65, "a axial" should read -- an axial --.

<u>Column 3,</u>
Line 2, "th o" should read -- the two --.

<u>Column 6,</u>
Line 6, "tow" should read -- two --.

Signed and Sealed this

Fifteenth Day of July, 2003

JAMES E. ROGAN
*Director of the United States Patent and Trademark Office*